US009284526B2

(12) United States Patent
Olivieri et al.

(10) Patent No.: US 9,284,526 B2
(45) Date of Patent: Mar. 15, 2016

(54) CULTURE MEDIUM WITH YEAST OR SOY BEAN EXTRACT AS AMINO ACID SOURCE AND NO PROTEIN COMPLEXES OF ANIMAL ORIGIN

(75) Inventors: Roberto Olivieri, Siena (IT); Fabio Sabbatini, Monteroni d'Arbia (IT); Maria Kontakou, Caserta (IT); Lucia Tagliaferri, Siena (IT); Antonella Giglioli, Siena (IT); Rino Rappuoli, Monteriggioni (IT)

(73) Assignee: GSK Vaccines S.R.L., Siena (IT)

( * ) Notice: Subject to any disclaimer, the term of this patent is extended or adjusted under 35 U.S.C. 154(b) by 1510 days.

(21) Appl. No.: 10/979,758

(22) Filed: Nov. 3, 2004

(65) Prior Publication Data
US 2005/0089968 A1   Apr. 28, 2005

Related U.S. Application Data

(63) Continuation of application No. 10/383,001, filed on Mar. 7, 2003, now abandoned, which is a continuation of application No. 09/424,800, filed on Feb. 24, 2000, application No. PCT/IB98/00938, filed on May 28, 1998, now abandoned.

(30) Foreign Application Priority Data

May 28, 1997 (GB) .................................... 9710981.3
Mar. 30, 1998 (GB) .................................... 9806802.6

(51) Int. Cl.
C12N 1/20 (2006.01)
C12R 1/21 (2006.01)

(52) U.S. Cl.
CPC .... C12N 1/20 (2013.01); C12R 1/21 (2013.01)

(58) Field of Classification Search
USPC ..................................................... 435/253.6
See application file for complete search history.

(56) References Cited

U.S. PATENT DOCUMENTS

| 3,912,822 | A | * | 10/1975 | Yokotsuka et al. | .............. | 426/44 |
| 4,115,591 | A | * | 9/1978 | Noda et al. | .......................... | 426/7 |
| 4,695,624 | A | * | 9/1987 | Marburg et al. | .......... | 424/197.11 |
| 5,494,808 | A | | 2/1996 | Fu | | |

FOREIGN PATENT DOCUMENTS

| CA | 2099632 | | 6/1993 |
| EP | 0429816 | | 6/1991 |
| EP | 0540897 | A1 | 9/1992 |
| EP | 5759510 | A2 | 12/1993 |
| EP | 0624376 | A1 | 11/1994 |
| WO | 9409115 | A1 | 4/1994 |
| WO | WO 94/09115 | * | 4/1994 |
| WO | 96/13576 | A1 | 5/1996 |
| WO | 96/14086 | A1 | 5/1996 |
| WO | 9614393 | A1 | 5/1996 |

OTHER PUBLICATIONS

Kim et al. The Journal of Biological Chemistry. 1996, vol. 271, No. 26, pp. 15549-15557.*
L. O. Butler, "A Defined Medium for Haemophilus Influenzae and Haemophilus parainfluenzae," Journal of General Microbiology, vol. 27 pp. 51-60 (1962).
Carty et al., "Fermentation Studies with Haemophilus Influenzae," from Developments in Industrial Microbiology, Chapter 63 pp. 763-767 (1985), published by the Society for Industrial Microbiology.
Michael J. Corbel, "Control Testing of Combined Vaccines. A Consideration of Potential Problems and Approaches," Biologicals, vol. 22, pp. 353-360 (1994).
Herriott et al., "Defined Medium for Growth of Haemophilus Influenzae," Journal of Bacteriology, vol. 101, No. 2.
Klein et al., "Simplified Media for the Growth of Haemophilus Influenzae from Clinical and Normal Flora Sources," Journal of General Microbiology, vol. 113, pp. 409-411 (1979).
Lucas et al., "An Idiotypic Marker Associated with a Germ-line Encoded k Light Chain Variable Region that Predominates the Vaccine-induced Human Antibody Response to the Haemophilus influenzae b Polysaccharide," Journal of Clinical Investigation, vol. 88, pp. 1811-1818, (1991).
Marchini et al., "Optimized Conditions for the Fermentation of Helicobacter Pylori and Production of Vacuolating Cytotoxin," FEMS Microbiology Letters, vol. 124, No. 1 pp. 55-59 (1994).
Marchini et al., "Cyclodextrins for Growth of Helicobacter Pylori and Production of Vacuolating Cytotoxin", Archives of Microbiology, vol. 164, No. 4 pp. 290-293 (1995).
Nahm et al., "Functional Capacities of Clonal Antibodies to Haemophilus influenzae Type b Polysaccharide," Infection and Immunity, vol. 63, No. 8, pp. 2989-2994 (1995).
Pienta et al., "ATCC Bacteria and Bacteriophages, 19th Edition," pp. 71, 103, 108, 109, 177, 178, 183, 249, 250, 477-479, 488 and 507 (1996).
Vella et al., "Immunogenicity of New Haemophilus influenzae Type b Conjugate Vaccine (Meningococcal Protein Conjugate) (PedvaxHIB)" Pediatrics pp. 668-675 (1990).
Harold L. Wolin, "Defined Medium for Haemophilus Influenzae Type B," Journal of Bacteriology, vol. 85, pp. 253-254, (1963).
Buck, G. et al. "Medium Supplementation for Growth of Campylobacter pyloridis," Journal of Clinical Microbiology, vol. 25, No. 4, 1987, pp. 597-599.
Nedenskov, P. "Nutritional Requirements for Growth of Helicobacter pylori," Applied and Environmental Microbiology, vol. 60, No. 9, 1994, pp. 3450-3453.
Reynolds, D. "Defined Media for H. Pylon," Methods in Molecular Medicine; Helicobacter Pylon Protocols Humana Press Inc., 1997, pp. 53-61.
Stark, R. et al. "Amino acid utilisation and deamination of glutamine and asparagine by Helicobacter pylori," Journal of Medical Microbiology, vol. 46, No. 47, 1997, pp. 793-800.

(Continued)

*Primary Examiner* — Vera Afremova
(74) *Attorney, Agent, or Firm* — Helen Lee; Virginia Campen

(57) ABSTRACT

The present invention relates to a medium containing non-animal derived proteinaceous material for cultivating patheogenic bacteria to produce an immunogenic factor and processes employing such medium.

4 Claims, 8 Drawing Sheets

(56) References Cited

OTHER PUBLICATIONS

Walsh, E. et al. "Influence of medium composition on the growth and antigen expression of Helicobacter pylon," Journal of Applied Microbiology, vol. 83, No. 1, 1997, pp. 67-75.

Frasch, C. "Production and Control of Neisseria meningitidis Vaccines," Advances in Biotechnological Processes, vol. 13, No. 1, 1990, pp. 123-145.

Fu, J. et al. "Recent advances in the large scale fermentation of Neisseria meningitidis group B for the production of an outer membrane protein complex," Bio/technology, vol. 13, No. 2, 1995, pp. 170-174.

Wesley, C. "Nutritional profiles of Neisseria gonorrhoeae, Neisseria meningitidis, and Neisseria lactamica in chemically defined media and the use of growth requirements for gonococcal typing," Journal of Infectious Diseases, vol. 128, No. 2, 1973, pp. 178-194.

Kenny, C. et al. "A chemically defined protein-free liquid medium for the cultivation of some species of Neisseria," Bulletin of the World Health Organization, vol. 37, No. 4, 1967, pp. 569-573.

"ATCC: Bacteria and Viruses. 19th Edition," 1996, ATCC, Eds. Pienta, P. et al. XP002451189.

Anderson et al. (1977). "Isolation of the capsular polysaccharide from culture supernatant of Haemophilus influenzae type b," Infect. Immun. 15(2):472-477.

Takagi et al. (2003). "Characterization of polysaccharide production of Haemophilus influenzae type b and its relationship to bacterial cell growth," App Biochem Biotechnol 110:91-100.

Takagi et al. (2006). "Improved cultivation conditions for polysaccharide production by H. influenzae type b," J Chem Technol Biotechnol 81:182-188.

Butler (1962). "A Defined Medium for Haemophilus influenzae and Haemophilus parainfluenzae," Microbiology 27(1): 51-60.

Corbel (1994). "Control testing of combined vaccines: a consideration of potential problems and approaches," Biologicals. 22(4):353-60.

Klein et al. (1979). "Simplified media for the growth of Haemophilus influenzae from clinical and normal flora sources," J Gen Microbiol. 113(2):409-11.

Schneerson et al. (1996). "A toxoid vaccine for pertussis as well as diphtheria? Lessons to be relearned," Lancet. 348(9037):1289-92.

Stainer et al. (1973). "The production of high potency diphtheria toxin in submerged culture in relatively simple equipment using a semisynthetic medium," Biotechnol Bioeng Symp. 0(4-1):283-93.

Taha et al. (1985). "Soybean extracts as culture media for the growth and toxin production of Corynebacterium diphtheriae," J Egypt Public Health Assoc.60(1-2):113-26.

Wolin (1963). "Defined Medium for Haemophilus Influenzae Type B," J Bacteriol. 85(1): 253-254.

* cited by examiner

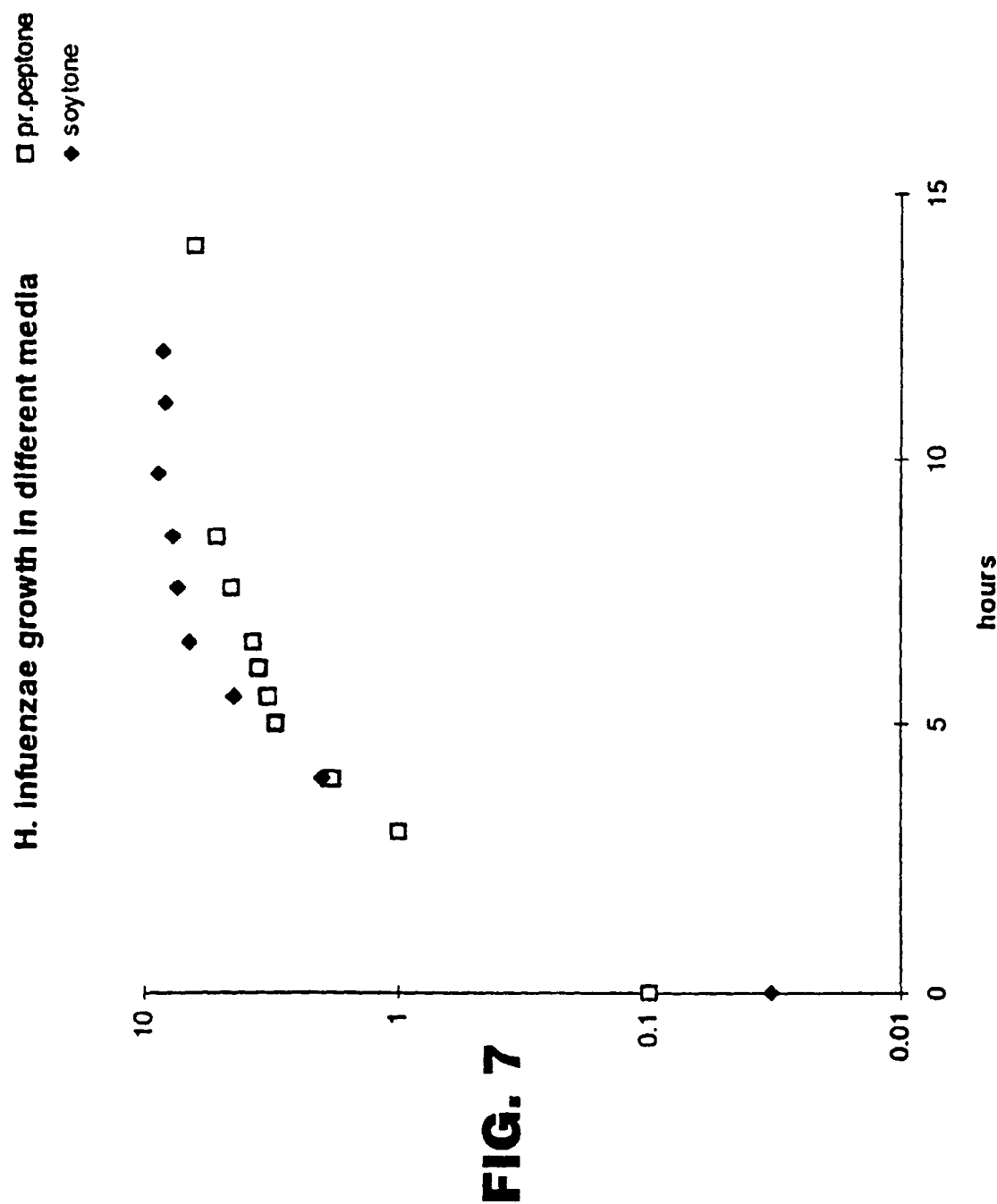

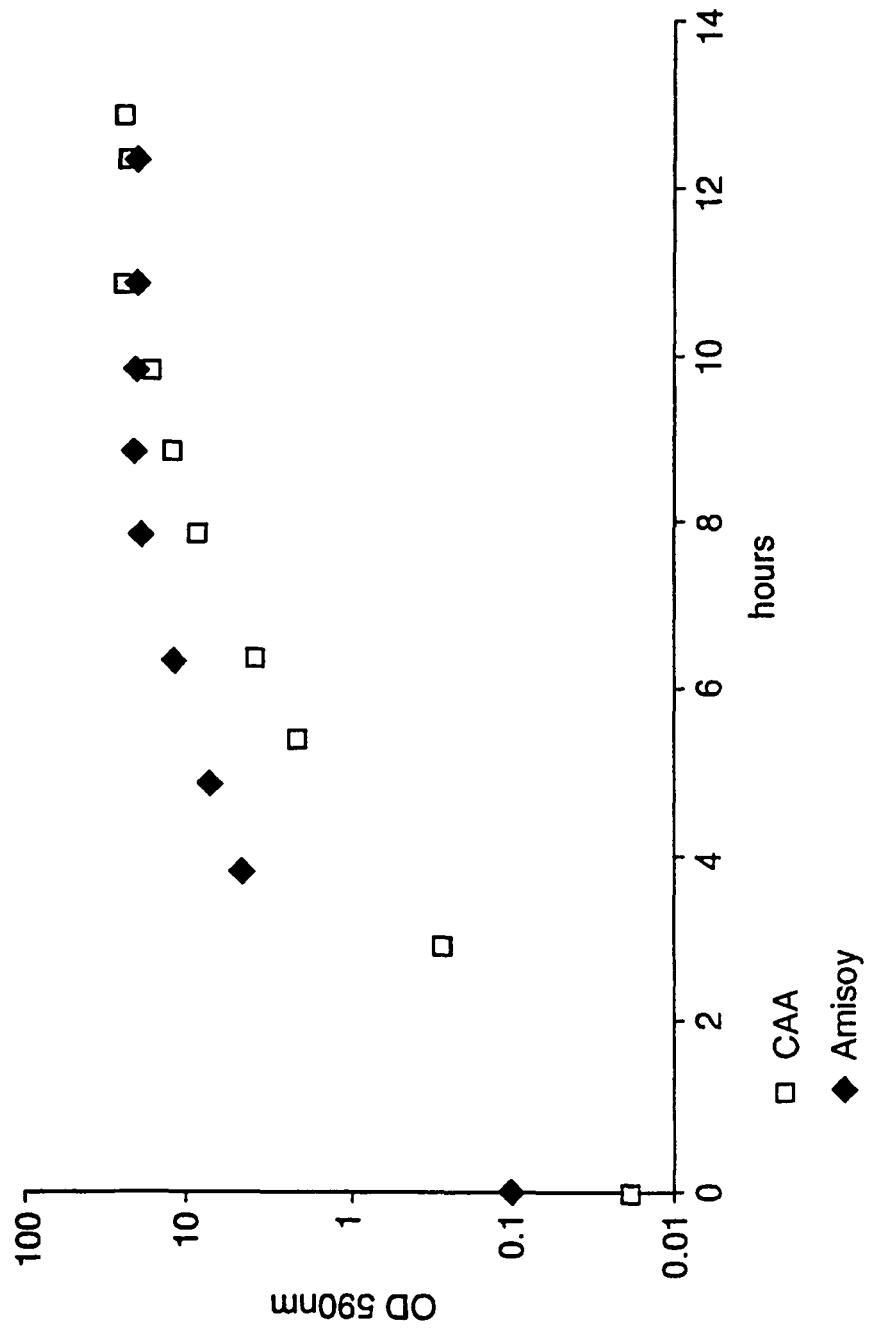

CULTURE MEDIUM WITH YEAST OR SOY BEAN EXTRACT AS AMINO ACID SOURCE AND NO PROTEIN COMPLEXES OF ANIMAL ORIGIN

The present invention relates to a medium for cultivating pathogenic bacteria. The present invention also relates to the use of the medium to cultivate pathogenic bacteria, obtaining immunogenic factors from the bacteria being cultivated and preparing vaccines using the immunogenic factors.

Bacterial vaccines are produced by cultivating pathogenic bacteria in a medium, isolating immunogenic factors and preparing vaccines based on the isolated immunogenic factors. Such methods are described in Bacterial Vaccines, 1984, Ed. Rene Germanier Academic Press and Bacterial Vaccines in Advances in Biotechnology Processes, Vol. 13, 1990, Ed. A. Mizrahi, Wiley-Liss. In conventional methods, the pathogenic bacteria are cultivated in media containing proteinaceous material of animal origin. These compounds are used in the belief that some growth factors, essential for the growth of pathogenic bacteria, were only present in compounds of animal origin such as blood, brain heart infusion, meat, etc. For instance, *C. tetani* is grown in media containing a heart infusion and an enzymatic digest of casein; *C. diphtheriae* requires a beef infusion; *H. pylori* is grown in media containing pentamine and tryptone; and *Haemophilus influenzae* is grown in media containing proteose peptones. World Health Organisation report series numbers 800 (1990) and 814 (1991) indicate that to grow *Haemophilus influenza, Corynebacterium diphtheriae, clostridium tetani* and *Bordetella pertussis*, media comprising compounds of animal origin are required.

The requirement for proteinaceous material of animal origin in the media gives rise to concern over possible contamination of the media. In particular, concern that the media may be contaminated with the bovine spongiform encephalopathy (BSE) causative agent or other infectious and harmful agents, restricts the usefulness of any factors derived from such cultures, especially in therapeutic applications.

It has surprisingly been found that proteinaceous materials of non-animal origin are able to sustain the growth of pathogenic bacteria and enable the production of immunogenic factors by the bacteria.

In patent application DD 294 502-A, a process for preparing soya hydrolysates and the use of the soya hydrolysates in culturing microorganisms for fimbriae is disclosed. The soya hydrolysate is prepared by culturing soya-flour-containing medium with streptomyces strains. The soya hydrolysate is used as a carbon source due to the high percentage of polysaccharides present and contains less than 20% by dry weight protein.

The use of proteinaceous material of non-animal origin, such as proteins from soy beans, cotton seeds, potatoes, etc., as a media constituent for the cultivation of pathogenic bacteria, completely removes the risk of animal derived contamination, such as BSE, being transmitted into humans in any subsequent therapeutic or prophylactic applications.

A further advantage associated with the use of vegetable derived proteinaceous materials is the reduction in cost of producing the materials and the increased consistency in the materials (non-animal derived proteinaceous material is more uniform in its composition than animal derived materials).

The present invention provides a medium for cultivating pathogenic bacteria to produce an immunogenic factor wherein the medium comprises at least 20% by dry weight of a non-animal derived proteinaceous material, and does not comprise animal derived proteinaceous material.

Any standard medium for cultivating bacteria may be used as the basis for the medium of the present invention, provided the medium does not contain animal derived proteinaceous material.

Preferably, the medium of the present invention comprises a carbon and an energy source, a nitrogen source, essential salts and optionally a selecting agent, such as an antibiotic, for selecting the microorganisms to be cultured.

The medium of the present invention may be a solid or liquid medium. Examples of standard liquid media which may form the basis of the medium of the present invention include Brucella Broth (without tryptone and peptamine), Watson medium (without casamino acids), Mueller Miller medium (without heart infusion and casein hydrolysate), CL medium (without casamino acids) and Franz A medium. Standard solid media can be prepared from any of the liquid media by the addition of a solidifying agent such as agar.

The term "cultivating" as used herein means the maintenance of, and preferably the growth of, bacteria. Bacterial growth is herein defined as an increase in bacterial biomass.

The term "pathogenic bacteria" as used herein, means any bacteria which is involved in the pathogenesis of a disease. Preferred pathogenic bacteria include *Helicobacter pylori, Haemophilus influenzae, Corynebacterium diphtheriae* and *Neisseria meningitidis, Bordetella pertussis* and *Clostridium tetani*.

The term "immunogenic factor" as used herein, means any factor which is capable of stimulating the immune system of a human or animal. Such immunogenic factors include antigenic proteins and especially virulence factors and fragments thereof. Virulence factors are defined as being associated with the virulence of a bacteria and includes such factors as the vaculating cytotoxin VacA produced by *Helicobacter pylori*. Other virulent factors are described by Rappuoli, R. et al., European Journal of Gastroenterology and Hepatology of *Helicobacterpylori* infection. Proceedings of an interdisciplinary meeting (Genova, Jun. 18-19, 1993) J. J. Misiewicz, Ed. (CS Current Science), pp S76-S78 (incorporated herein by reference). The immunogenic factor may be genetically detoxified or treated by a toxoiding process. Methods for genetically detoxifying and toxoiding immunogenic factors are well known to those skilled in the art and include those described by Rappuoli, R., Vaccine, 12, 579-581, (1994) (herein incorporated by reference).

The term "proteinaceous material", as used herein, means proteins and protein degradation products including free amino acids. Preferably, the proteinaceous material is a protein hydrolysate.

Non-animal derived proteinaceous materials as used herein means proteinaceous materials derived from non-mammalian sources, such as vegetables, birds, fish, yeasts, funghi, algae and microorganisms. More preferably, non-animal proteinaceous materials mean proteinaceous material derived from vegetables, yeasts, algae and microorganisms. Most preferably, non-animal derived proteinaceous materials means proteinaceous materials derived from vegetables such as protein compositions derived from soy beans, cotton seeds, potatoes, etc.

Preferred non-animal derived proteinaceous materials include yeast extracts such as HY YEST (Quest) and soy bean derived protein compositions such as Hysoy (Quest), Amisoy (Quest), N-Z soy (Quest) and Soytone (Difco).

Yeast extracts can be prepared by standard procedures well known to those skilled in the art. Furthermore, yeast extracts are commercially available from numerous sources including Sigma and Quest.

Soy bean derived protein compositions can be prepared by enzymatic digestion of soy bean meal or soy isolate using standard enzymes such as papain. For example, N-Z soy is a soluble protein composition made by the enzymatic digestion of a soy isolate and Hysoy is a papaic digest of soy bean meal. Soy bean derived protein compositions can also be obtained by acid hydrolysis of a soy isolate. For example, Amisoy is a source of amino acids and peptides produced by acid hydrolysis of a soy isolate.

Other non-animal derived proteinaceous materials can be obtained by either enzymatic digestion or by acid hydrolysis of a protein containing material of a non-mammalian source.

The non-animal derived proteinaceous material in the medium of the present invention may comprise two or more different non-animal derived proteinaceous materials, such as a mixture of soy bean derived protein compositions such as Hysoy, Amisoy, N-Z soy and Soytone.

Animal derived proteinaceous materials include protein compositions such as fetal calf serum (FCS), bovine serum albumin (BSA), proteose peptones, casamino acids, tryptone, peptamin and casein hydrolyzates.

Preferably, the medium of the present invention comprises at least 20% by dry weight of a non-animal derived proteinaceous material, more preferably, at least 30% by dry weight of a non-animal derived proteinaceous material and most preferably at least 50% by dry weight of a non-animal derived proteinaceous material.

It has surprisingly been found that the cultivation of pathogenic bacteria using the medium of the present invention results in increased growth of the bacteria and an increased yield of immunogenic factors compared to cultivation of the pathogenic bacteria in a medium containing animal derived proteinaceous material.

The present invention further provides a process for making a medium for cultivating pathogenic bacteria to produce an immunogenic factor comprising adding sufficient non-animal derived proteinaceous material to a standard medium for cultivating bacteria, which does not comprise animal derived proteinaceous material, so that the medium for cultivating pathogenic bacteria comprises at least 20% by dry weight of the non-animal derived proteinaceous material, and does not comprise animal derived proteinaceous material.

Examples of standard liquid media include Brucella Broth (without tryptone and peptamine) Watson medium (without casamino acids), Mueller Miller medium (without heart infusion and casein hydrolysate), CL medium (without casamino acids) and Franz A medium. Standard solid media can be prepared from any of the liquid media by the addition of a solidifying agent such as agar.

The present invention further provides a culture comprising the medium of any of the previous claims and pathogenic bacteria. Preferred pathogenic bacteria include *Helicobacter pylori, Haemophilus influenzae, Corynebacterium diphtheriae* and *Neisseria meningitidis, Bordetella pertussis* and *Clostridium tetani*. Most preferably, the pathogenic bacterium is *Helicobacter pylori*.

The present invention also provides a process for preparing an immunogenic factor of a pathogenic bacteria comprising the steps of cultivating the bacteria in the medium of the present invention and optionally purifying the immunogenic factor from the medium.

Preferably, the pathogenic bacteria are cultured in the medium of the present invention for at least 6 hours, more preferably at least 36 hours, and most preferably at least 72 hours under suitable conditions for the production of the immunogenic factor.

Suitable culture conditions for the production of the immunogenic factor, including the duration of the culture, will vary depending on the bacteria being cultured. However, one skilled in the art can easily determine the culture conditions required for the production of the immunogenic factor by following standard protocols, such as those described in the series Methods in Microbiology, Academic Press Inc., (incorporated herein by reference) and, if necessary, by performing a number of standard experiments to determine suitable culture conditions.

The immunogenic factor can be isolated from the bacterial culture using a number of standard techniques including those described by Manetti, R. et al., Infect. Immun., 63, 4476-4480, (1995), incorporated herein by reference.

The present invention also provides a process for the production of a vaccine comprising preparing an immunogenic factor of a pathogenic bacteria comprising the steps of cultivating the bacteria in the medium of the present invention, optionally purifying the immunogenic factor from the medium and bringing said factor, optionally toxoided, into association with a pharmaceutically acceptable carrier. Suitable methods for producing a vaccine are described by Rappuoli, R., New and improved vaccines against Diphtheria and Tetanus. (1990), 251-268, New Generation of Vaccines, Ed. G. C. Woodrow, M. M Levine, Marcel Dekker Inc. New York. (Incorporated herein by reference).

The vaccines prepared by the process of the present invention will require the addition of adjuvants when they are used. Suitable adjuvants are described in Gupta, R. K. et al., Vaccine, 13, 1263-1276, (1995).

The vaccines prepared by the process of the present invention can be used to vaccinate an individual against a bacterial infection. Preferred bacterial infections which can be vaccinated against include type B gastritis, bacterial meningitidis, diphtheria, tetanus and whooping cough.

The vaccines prepared by the process of the present invention may be provided as a pharmaceutical composition comprising the vaccine of the present invention in admixture with a pharmaceutically acceptable carrier and adjuvants as mentioned above.

The vaccines prepared by the process of the present invention can be administered by oral or parenteral route, including intravenous, intramuscular, intraperitoneal, subcuaneous, transdermal, airway (aerosol), rectal and topical administration.

For oral administration, the compounds of the invention will generally be provided in the form of tablets or capsules or as an aqueous solution or suspension.

Tablets for oral use may include the active ingredients (the vaccine component) mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and other well known agents, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard capsules on which the active ingredient is mixed with a solid diluent, and soft capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The vaccines prepared by the process of the present invention may also be presented as liposome formulations.

The present invention is now described with reference to the following examples and to the figures in which.

Figure 4:
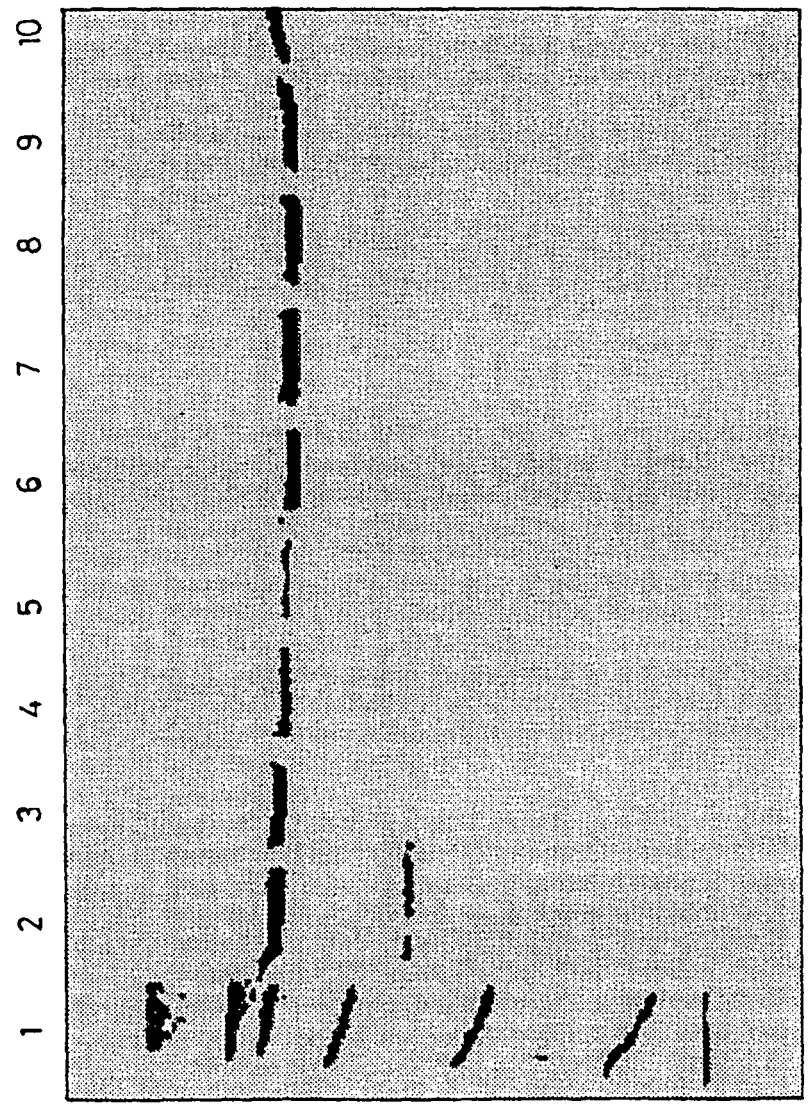

FIG. 4 shows a VacA immunoblot wherein lane 1 is molecular weight marker, lane 2 VacA standard 750 ng, lane 3 VacA standard 500 ng, lane 4 VacA standard 400 ng, lane 5 VacA standard 150 ng, lane 6 VacA standard 20 ng, lane 7 VacA produced at the end of fermentation, lane 8 VacA produced after 48 hours of culture, lane 9 VacA produced after 30 hours of culture, lane 10 VacA produced after 23 hours of culture.

Figure 5:
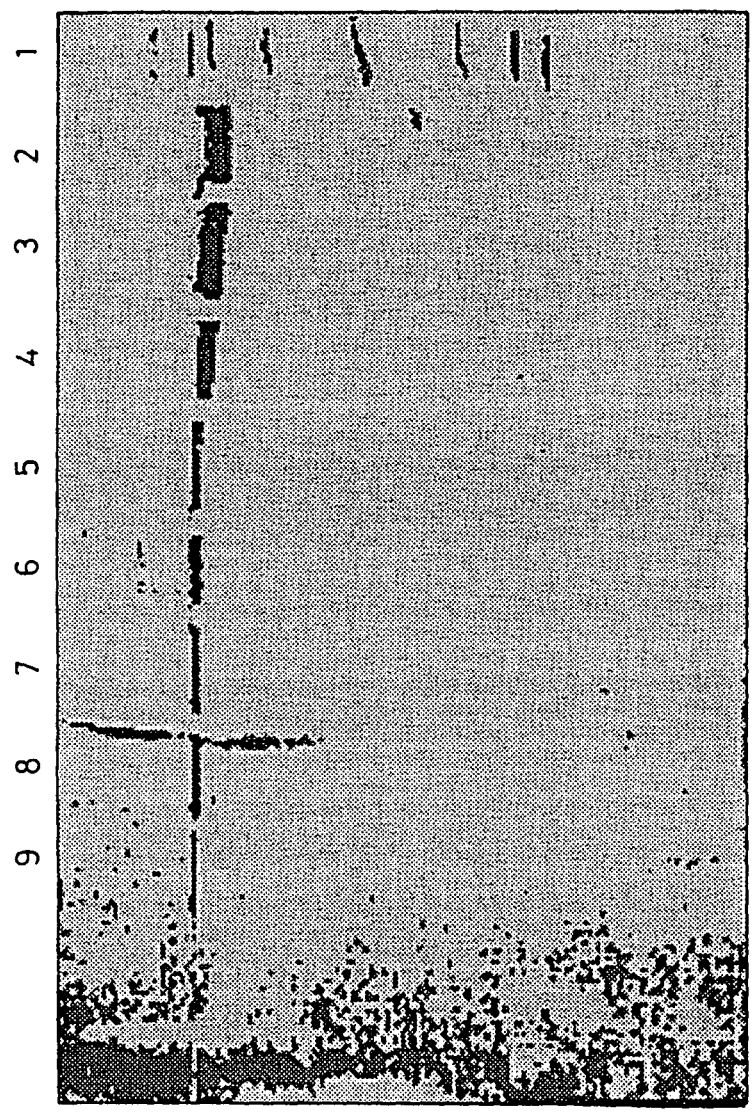

FIG. 5 shows a VacA immunoblot wherein lane 1 is molecular weight marker, lane 2 VacA standard 750 ng, lane 3 VacA standard 500 ng, lane 4 VacA standard 400 ng, lane 5 VacA standard 150 ng, lane 6 VacA standard 20 ng, lane 7 VacA produced at the end of fermentation, lane 8 VacA produced after 31.5 hours of culture, lane 9 VacA produced after 30 hours of culture, lane 10 VacA produced after 24 hours of culture.

Figure 6:
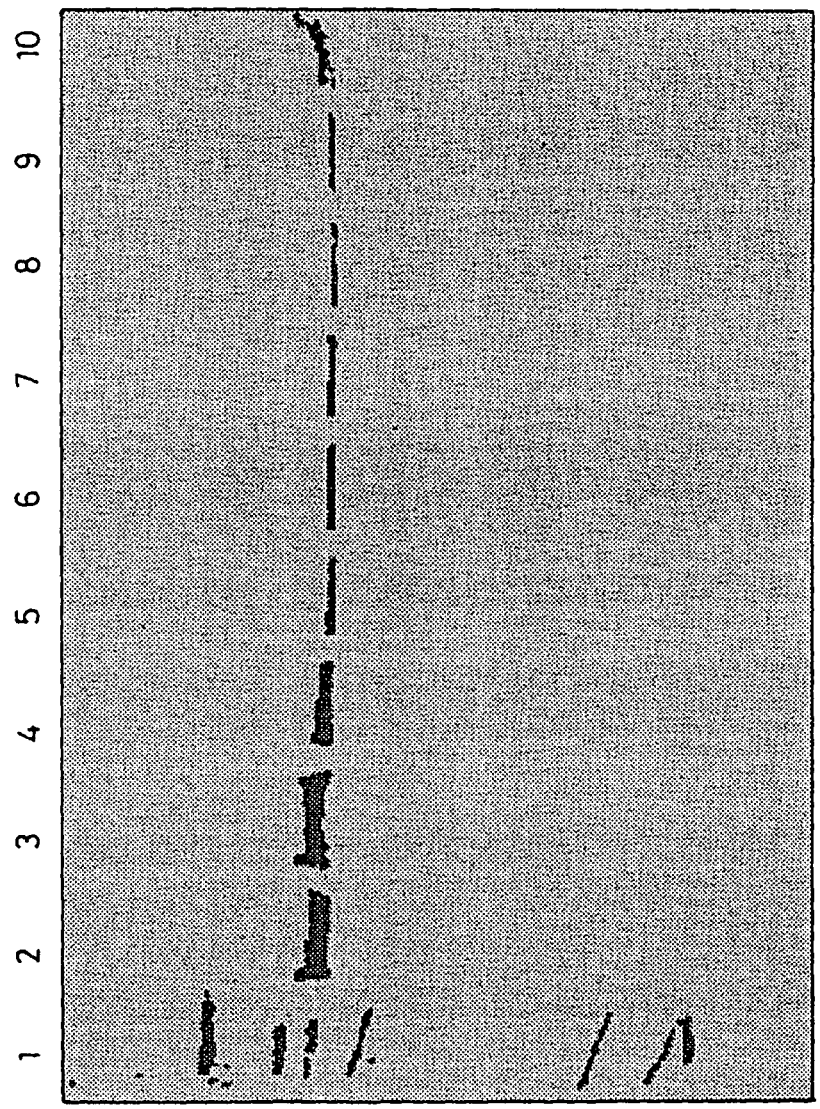

FIG. 6 shows a VacA immunoblot wherein lane 1 is molecular weight marker, lane 2 VacA standard 750 ng, lane 3 VacA standard 500 ng, lane 4 VacA standard 400 ng, lane 5 VacA standard 20 ng, lane 6 VacA produced at the end of fermentation, lane 7 VacA produced after 48 hours of culture, lane 8 VacA produced after 31 hours of culture, lane 9 VacA produced after 24.5 hours of culture, lane 10 VacA standard 150 ng.

FIG. 7 shows the kinetics of growth of *H. influenzae* b in simplified Franz medium containing Soytone or Proteose peptone.

FIG. 8 shows the kinetics of growth of *N. meningitidis* C in Watson medium containing Casaminoacids or Amisoy.

EXAMPLES

All references are herein incorporated by reference.

Example I

*Helicobacter pylori* is a curved gram-negative microaerobic bacterium isolated about 10 years ago and is associated with type B gastritis in humans. This bacterium colonizes the human gastric mucosa and establishes a chronic infection that may result in gastric and duodenal ulcers (Blaser, M. J., (1990), J. Infect. Dis., 161, 629-633) and can be a risk factor for the development of gastric carcinoma (Parsonnet, J. et al., (1991), New Engl. J. Med., 325, 1127-1131).

In the long term, the infection and the diseases could be prevented and treated by vaccination. Currently, several factors involved in bacterial adhesion, colonisation and virulence have been identified. One of the most interesting factors involved in the disease is the vacuolating cytotoxin (VacA) that causes massive vacuolization in several mammalian cell lines (Leunk, R. D., (1991), Rev. Infect. Dis., 13(suppl.8), S683-S689). Vacuoles have also been observed in the gastric epithelia of patients with chronic gastritis (Tricottet, V. et al., (1986), Ultrastruct. Pathol., 10, 113-117). This protein has been shown to cause ulceration in mice (Telford, J. L. et al., (1994), J. Exp. Med., 179, 1653-1658) and is a vaccine candidate. The purified cytotoxin is a protein of 87-94 kD that can be purified in very small amounts from bacterial culture supernatant.

Material and Methods
Bacterial Strain.

The *Helicobacter pylori* CCUG 17874 (type strain, Culture Collection, University of Goteborg) was used.

Media and Supplements.

Brucella Broth (tryptone 10 g $l^{-1}$, peptamin 10 g $l^{-1}$, dextrose 1 g $l^{-1}$, yeast extract 2 g $l^{-1}$, sodium chloride 5 g $l^{-1}$ and sodium bisulfite 0.1 g $l^{-1}$) (BB)(Difco) supplemented with 2 g $l^{-1}$ of (2,6 di-0-methyl)-b-cyclodextrin (CD) (Teijin Lim. Tokyo, Japan) and 20 mg/L of streptomycin was used as liquid medium for comparison purpose. Hysoy or Soytone were used at a concentration of 10 g/L instead of tryptone and peptamin present in BB.

Preservation.

Frozen aliquots for inocula were prepared from flask cultures of $2 \times 10^8$ CFU $ml^{-1}$ diluted 1:2 with a solution composed of glycerol 40%, fetal calf serum (FCS) (HyClone, Logan, Utah) 20% and 0.4% CD. The suspension obtained was distributed in 3 ml vials and stored at −80° C. and used as starting frozen vials for comparison with new frozen vials prepared substituting FCS with Soytone 20%.

Growth in Liquid Medium.

Initial cultures were performed in 500 ml Erlenmeyer flasks containing 100 ml of liquid medium. Cultures were inoculated with 3 ml of frozen stocks and incubated at 36° C. for 36 hours with shaking (100 rpm, 2.5 cm throw) in a microaerobic environment. Flasks were placed inside an anaerobic jar where BBL Campy Pak envelopes (Becton Dickinson) were used to generate the proper conditions. These cultures were then used to inoculate 1000 ml flasks containing 250 ml of medium and incubated in the same conditions mentioned above and used to inoculate the bioreactors.

Culture Vessels and Growth Conditions.

Batch fermentations were carried out in 7 liters bioreactors (MBR Bioreactors AG, 8620 Wetzikon, C H) containing 5 l of medium. All cultures were grown at 36° C. The pH values were not controlled. The dissolved oxygen tension (DOT) was maintained automatically at the pre-set level (3%) by a two step procedure. First, air flow rate was increased from 0.1 up to 0.5 l $l^{-1}$ $min^{-1}$ to satisfy the increasing $O_2$ demand of the culture. If further increases were necessary, they were obtained by supplying pure $O_2$ up to a maximum of 0.4 l $l^{-1}$ $min^{-1}$. During the first 12 hours of growth, a constant flow of $N_2$ and $CO_2$ was maintained equal to 0.2 l $l^{-1}$ $min^{-1}$ and 0.02 l $l^{-1}$ $min^{-1}$ respectively. The agitation speed was maintained at 130 rpm. The agitator shaft was equipped with two Rhuston turbines having a diameter of 7 cm and the diameter of the bioreactor was 17 cm.

Glucose Feed.

A 50% glucose solution was added at time 0 to give a final concentration of 5 g/L. Another addition of 5 g/L was made when the OD was in a range 2-3.

Biomass Determination.

Growth was monitored by optical density at 590 nm against a water blank (Perkin Elmer 35 spectrophotometer), light path of 1 cm. Purity checks of the samples were made by Gram staining.

Analysis of the VacA Protein.

At determined time points during the fermentation, culture samples were centrifuged (Biofuge A, Heareus) at 8,300×g per 10 min. The supernatants were precipitated with trichloroacetic acid and subjected to 9% SDS-Page using a BioRad Mini Protean II apparatus. Proteins were transferred to nitrocellulose filters (Schleicher & Schuell) and then incubated overnight with polyclonal antisera raised against the VacA protein (Telford, J. L. et al., (1994), J. Exp. Med., 179, 1653-1658). After incubation for 2 hours with a horseradish-peroxidase conjugated secondary antibody (Sigma), the immunoreactive bands were visualized by 4-chloro-naphtol staining.

Results

Figure 1:
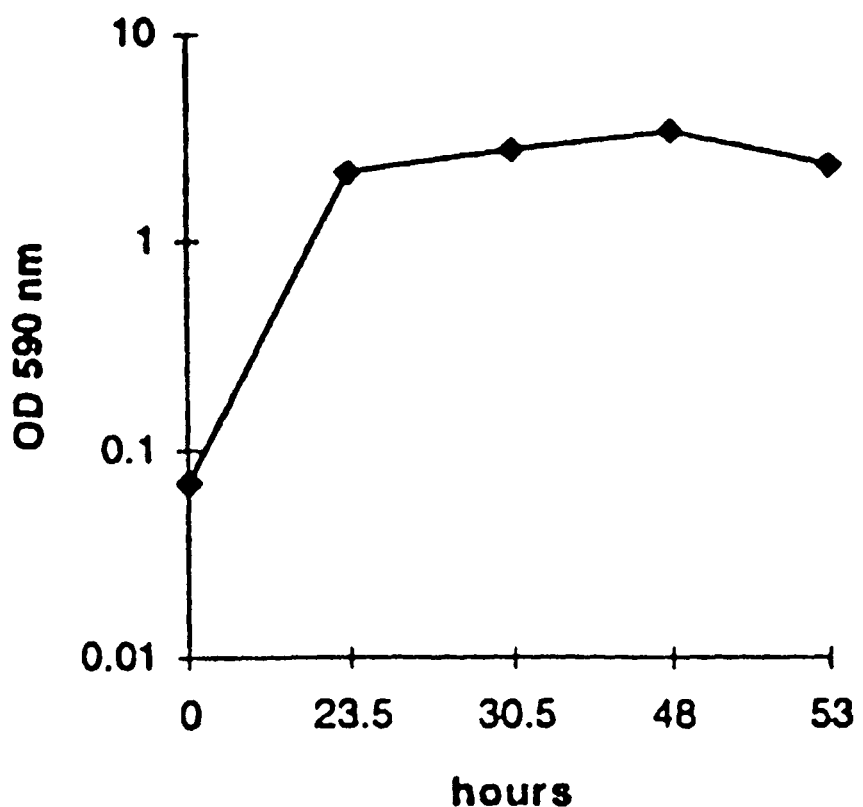
FIG. 1 shows the kinetics of growth of *H. pylori* CCUG 17874 in BB containing Tryptone and peptamin.

Brucella Broth is a complex medium composed of tryptone 10 g $l^{-1}$, peptamin 10 g $l^{-1}$, dextrose 1 g $ll^{-1}$, yeast extract 2 g $l^{-1}$, sodium chloride 5 g $l^{-1}$ and sodium bisulfite 0.1 g $l^{-1}$. This medium has been described in many articles as capable of supporting the growth of *H. pylori* only when supplemented with blood derivatives (Cover, T. L. and Blaser, M. J. (1992), J. Biol. Chem., 267, 10570-10575; Shahamat, M. et al., (1991), J. Clin. Microbiol., 29, 2835-2837; Buck, G. E. and Smith, J. S. (1987), J. Clin. Microbiol., 25, 597-599; and Morgan, D. R. et al., (1987), J. Clin. Microbiol., 25, 2123-2125). A substantial simplification of *H. pylori* growth media was obtained recently when it was discovered that cyclodextrins could be used in the place of blood derivatives (Olivieri, R. et al., (1993), J. Clin. Microbiol., 31, 160-162). The growth of *H. pylori* using this simplified medium and glucose feed is reported in FIG. 1. Glucose feeds were used to ensure that the carbon and energy source was always present in the medium.

When *H. pylori* was cultured in these conditions, the production of VacA in the medium was measured as described above. The results are shown in FIG. 5 and FIG. 6.

Figure 2:
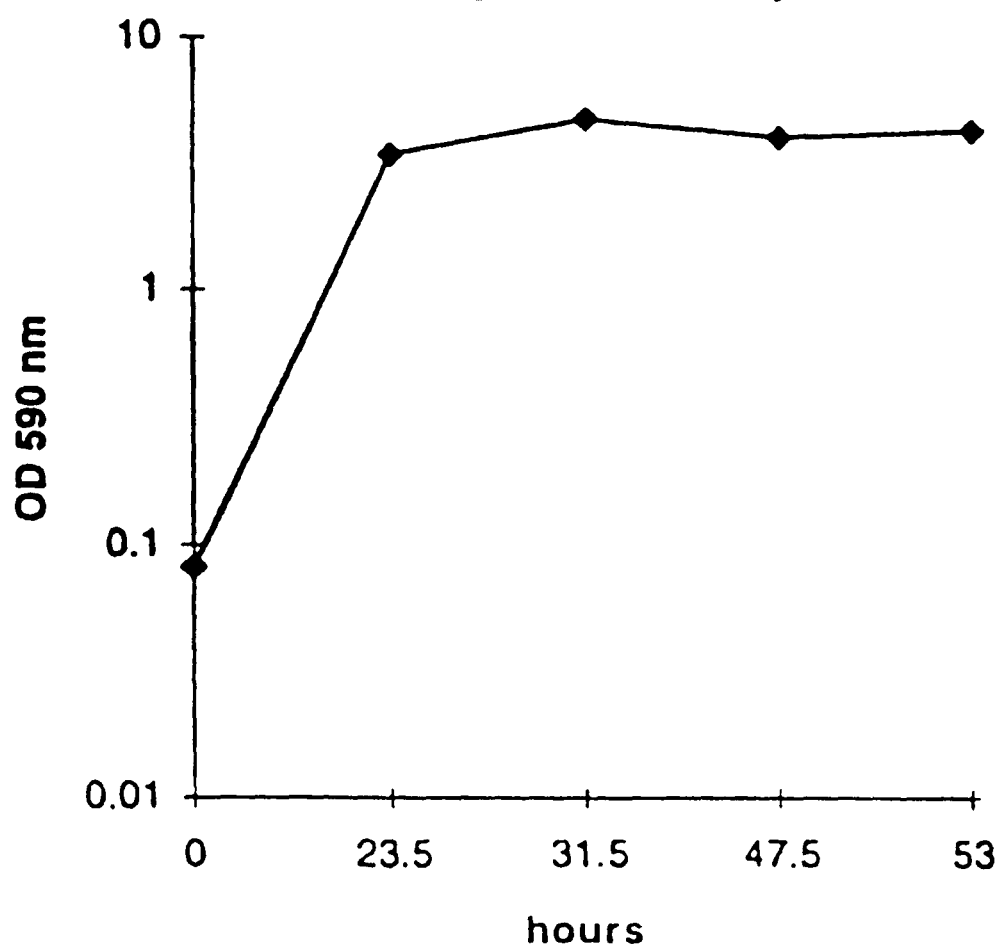
FIG. 2 shows the kinetics of growth of *H. pylori* CCUG 17874 in simplified BB containing Soytone.
Figure 3:
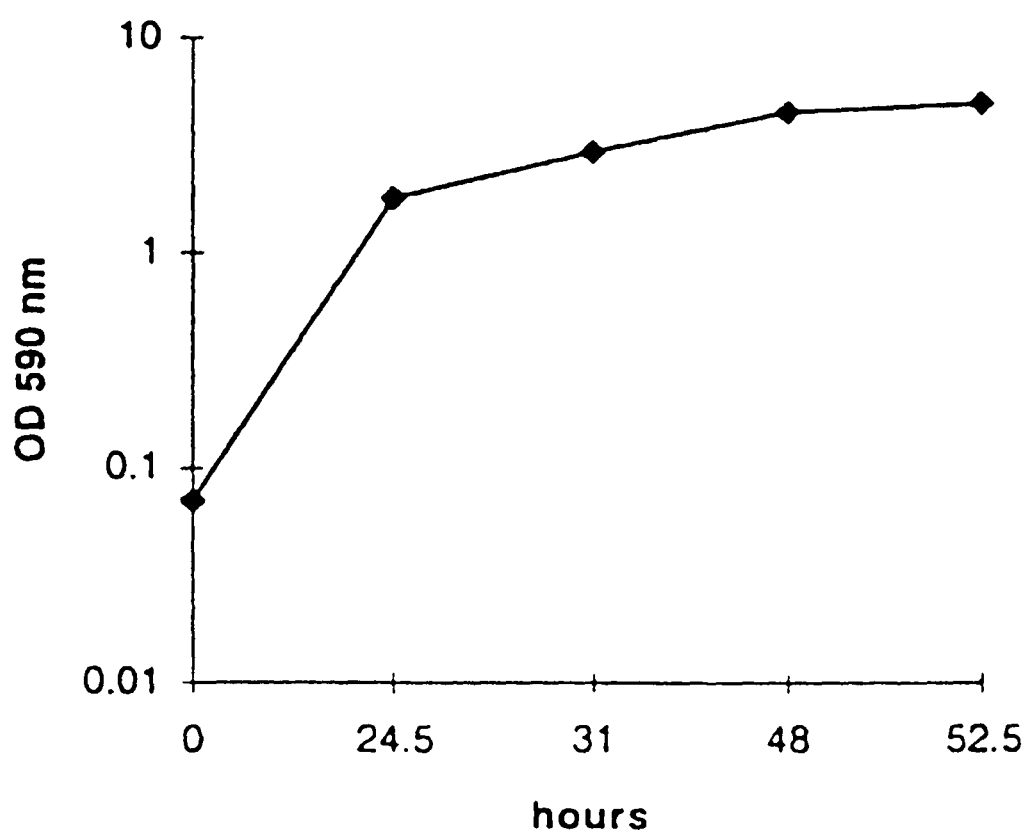
FIG. 3 shows the kinetics of growth *H. pylori* CCUG 17874 in simplified BB containing Hysoy.

The use of Soytone and Hysoy in the growth media gave the results reported in FIGS. 2 and 3 respectively. VacA production is reported in FIG. 5 when Soytone was used and in FIG. 6 when Hysoy was used.

The results show improvements to the growth media and fermentation conditions of *Helicobacter pylori* growth and in the production of the vacuolating cytotoxin (VacA).

Example II

*Haemophilus influenzae* are small, non motile, gram negative bacteria that are the major cause of bacterial meningitidis in children. These microorganisms are primarily invasive rather than toxigenic. They are inhabitants of the respiratory tract (commensal as well pathogenic) and they have antiphagocytic polysaccharides capsules.

Materials and Methods

Bacterial Strain

*Haemophilus influenzae* B ATCC 10211

Media and Supplements

The preparation of the media, involves use of different solutions as follows:

| "Franz A medium" Preparation | |
|---|---|
| Component | Amount per liter |
| Purified water | 800 mL |
| Glutamic acid | 1.6 g +/− 0.01 g |
| Na2HPO4 12H2O | 5.03 g +/− 0.05 g |
| KCl | 0.892 g +/− 0.008 g |
| NaCl | 6.005 g +/− 0.06 g |
| NH4Cl | 1.25 g +/− 0.01 g |
| Purified water | QS to 1.0 liter |
| 3N NaOH | as required for pH = 8.2. |

The above components are dissolved with mixing. 3N NaOH is used to pH the solution to pH=8.2

| Ultrafiltered Soytone preparation | |
|---|---|
| Component | Amount per liter |
| Soytone | 33.3 g +/− 0.03 g |
| Purified water | QS to 1.0 liter |

This solution was ultrafiltered through a 30 kD TFF apparatus.

| Ultrafiltered Proteose Peptone | |
|---|---|
| Component | Amount per liter |
| Proteose peptone | 33.3 g +/− 0.03 g |
| Purified water | QS to 1.0 liter |

This solution was ultrafiltered through a 30 kD TFF apparatus

| Ultrafiltered YE preparation | |
|---|---|
| Component | Amount per liter |
| yeast extract | 100 g +/− 0.02 g |
| Purified water | QS to 1.0 liter |

The yeast extract used was HY YEST available from Quest. The solution was ultrafiltered through a 10 kD TFF apparatus.

| 50% Glucose Solution | |
|---|---|
| Component | Amount per liter |
| glucose (anhydrous) | 500 g +/− 5 g |
| Purified water | QS to 1.0 liter |

| NAD 0.1% solution | |
|---|---|
| Component | Amount per liter |
| NAD | 1.0 g +/− 0.005 g |
| TRIS | 1.21 g +/− 0.01 g |
| Purified water | QS to 1.0 liter |
| HCl 37% | as required to pH 7.4 ± 0.2 |

| Hemin 0.4% solution | |
|---|---|
| Component | Amount per liter |
| Hemin | 4 g +/− 0.02 g |
| 0.2N NaOH | QS to 1.0 liter |

The hemin used is preferably chemically synthesised. Chemically synthesised hemin is commercially available from Fluka.

550 ml of Franz A was mixed with 450 ml of ultrafiltrated soytone or Proteose Peptone to obtain one liter of Hib basal medium which was sterilized by autoclaving at 121° C. for 30 minutes.

After cooling, 10 ml/L glucose solution, 20 ml/L of YE, 2 ml/L NAD solution, sterilized by filtration, were added (with the additions mentioned before) and the medium called "Hib Complete medium".

Growth in Liquid Media

Pre-warmed, unbaffeled shake flasks (500/150) were inoculated with 1.0 mL of a working stock vial each. The shake flasks were placed in an (1 inch throw) incubator-shaker at 35±1° C. at 150 RPM for 6 hours.

After 6 hours, the appropriate amount of the shake flask was transferred into one 2 L liter unbaffeled shake flask containing 0.5 L of pre-warmed "Hib complete medium". The shake flask was placed in an (1 inch throw) incubator-shaker at 35±1° C. at 200 rpm for 9 hours then the content was transferred into a sterile inoculation and the inoculate then transferred to the fermenter.

Culture Vessels and Growth Conditions

Batch fermentations were carried out in 30 liters bioreactors (MBR Bioreactors A G, 8620 Wetzikon, C H) containing 20 l of medium.

The cultures were growing at 35° C. and 2 psi back pressure. The pH was controlled to 7.3 with 3 N NaOH. The initial agitation rate was set at minimum of 150 rpm, and bottom aeration at 10 L/minute. DOT was maintained at 35% by rpm control in a range 150-400, then supplementing with oxygen if necessary. Antifoam was added manually to control foaming. Residual concentration of glucose was detected and when it was around 2 g/L, 0.2 liters of glucose solution were added.

Biomass Determination.

Growth was monitored by optical density at 590 nm against a water blank (Perkin Elmer 35 spectrophotometer), light path of 1 cm. Purity checks of the samples were made by Gram staining.

Analysis of Hib PS.

This analysis was performed by Rocket immuno electrophoresis as described by Weeke, B., Scand. J. Immunol. 2, 37-46, (1973), herein incorporated by reference.

Results

The growth curves obtained with Soytone and with Proteose peptone are compared in FIG. 7. The yield of Hib PS was 600 mg/L and 150 mg/L in the media containing Soytone and Proteose peptone respectively. Although the growth curves are quite similar using the two media, there is a four-fold increase in the yield of Hib PS using Soytone. The use of the culture media containing the vegetable derived proteinaceous material leads to an increased yield of polysaccharides, such as Hib PS, compared to the use of a culture medium containing animal derived proteinaceous material.

Example III

*C. diphtheriae* are gram positive, rod like microorganisms, which arrange themselves in palisades. *C. diphtheriae* lysogenization by a bacteriophage causes the synthesis of a potent toxin whose expression is regulated by iron concentration.

Materials and Methods

Bacterial Strain

*C. diphtheriae* CN 2000

Media and Supplements

The preparation of the media, involves use of different solutions as follows:

| A. Yeast Extract (YE) and Casamino Acids (CAA) Ultrafiltered | |
|---|---|
| Component | Amount g/L |
| Purified water | 800 ml |
| Yeast Extract | 20 g/L |
| Casamino Acids | 10 g/L |
| Purified water | QS to 1 L |

This solution was ultrafiltered through a 10 kD TFF apparatus and the permeate added to the deferration vessel.

| A.A Yeast Extract (YE) and Soytone Ultrafiltered | |
|---|---|
| Component | Amount g/L |
| Purified water | 800 ml |
| Yeast Extract | 20 g/L |
| Soytone | 10 g/L |
| Purified water | QS to 1 L |

This solution was ultrafiltered through a 10 kD TFF apparatus and the permeate added to the deferration vessel.

| A.B Yeast Extract Ultrafiltered | |
|---|---|
| Component | Amount g/L |
| Purified water | 800 ml |
| Yeast Extract | 30 g/l |
| Purified water | QS to 1 L |

This solution was ultrafiltered through a 10 kD TFF apparatus and the permeate added to the deferration vessel.

A.1 Deferration

The following components were introduced into an agitated vessel

| Component | Amount |
|---|---|
| UF (YE + CAA) solution | 1 L |
| $KH_2PO_4$ | 5 g/L |
| $CaCl_2$—$2H_2O$, 50% (w/v) | 2 mL/L |
| L-tryptophan, 1% (w/v) | 5 mL/L (0.05 g/L) |
| 3N NaOH | (enough to correct pH to 7.4) |

UF indicates that the solution is ultrafiltered.

With agitation, heat the solution to 100° C. Hold at 100° C. for 1 minute, then cool medium to 37° C. Filtration can commence once below 37° C. After filtration, the medium is described as "CY base medium with CAA".

A.1.A Deferration

The following components were introduced into an agitated vessel

| Component | Amount |
| --- | --- |
| UF (YE + Soytone) solution | 1 L |
| KH$_2$PO$_4$ | 5 g/L |
| CaCl$_2$—2H$_2$O, 50% (w/v) | 2 mL/L |
| L-tryptophan, 1% (w/v) | 5 mL/L (0.05 g/L) |
| 3N NaOH | (enough to correct pH to 7.4) |

With agitation, heat the solution to 100° C. Hold at 100° C. for 1 minute, then cool medium to 37° C. Filtration can commence once below 37° C. After filtration, the medium is described as "CY base medium with Soytone".

A.1.B Deferration

The following components were introduced into an agitated vessel

| Component | Amount |
| --- | --- |
| UF YE solution | 1 L |
| KH$_2$PO$_4$ | 5 g/L |
| CaCl$_2$—2H$_2$O, 50% (w/v) | 2 mL/L |
| L-tryptophan, 1% (w/v) | 5 mL/L (0.05 g/L) |
| 3N NaOH | (enough to correct pH to 7.4) |

With agitation, heat the solution to 100° C. Hold at 100° C. for 1 minute, then cool medium to 37° C. Filtration can commence once below 37° C. After filtration, the medium is described as "CY base medium with YE only".

B. "Supplements" Solution

| B1) Solution A ||
| --- | --- |
| Component | Amount per liter |
| MgSO$_4$—7H$_2$O | 225 g |
| Beta-alanine | 1.15 g |
| Nicotinic acid | 1.15 g |
| Pimelic acid | 0.075 g |
| CuSO$_4$ | 0.50 g |
| ZnSO$_4$—7H$_2$O | 0.40 g |
| MnCl$_2$—4H$_2$O | 0.15 g |
| HCl, 37% | 30 mL |
| Purified water | QS to 1.0 liters |

| B2) Solution B ||
| --- | --- |
| Component | Amount per liter |
| Purified water | 800 mL |
| L-cystine | 200 g |
| HCl, 37% | 200 mL |

The solutions are mixed individually for 10 minutes. After dissolution, 20 mL of Solution A and 10 mL of Solution B are mixed and filtered through a 0.2 micron filter. The solution is stored at 4° C. covered from light.

Flasks Sterilization

Once deferrated, filtered media (A.1 or A.1.A or A.1.B) are loaded into the flasks. Sterilize the flasks for 25 minutes at 121° C.

| Post-Sterilization Adjustments ||
| --- | --- |
| 1. Add "50% Maltose" | 30 ml/L |
| 2. Add "Supplements" | 3.0 ml/L |

Media with 1+2 above: "Complete CY medium with CAA or with Soytone or with YE only"

Growth in Liquid Media 500 ml unbaffeled shake flasks each with 100 ml of medium, were inoculated with 1.0 mL of a working stock vial.

The shake flasks were placed in an (1 inch throw) incubator-shaker at 35±1° C. at 100 rpm for 5 hours. After 5 hours, the agitation is increased to 250 rpm for 43 hours.

The process has two distinct phases: 1) Exponential growth), and 2) Production phase. The transition from the two phases is gradual and is marked by reductions in cell growth rate and oxygen demand.

Biomass Determination.

Growth was monitored by optical density at 590 nm against a water blank (Perkin Elmer 35 spectrophotometer), light path of 1 cm. Purity checks of the samples were made by Gram staining.

Results

After 48 hours of incubation, the OD and the Lf/ml in the flasks were:

| | | |
| --- | --- | --- |
| medium with CAA. | OD = 7.5 | Lf/ml = 50 |
| medium with Soytone. | OD = 7.87 | Lf/ml = 60 |
| medium with YE only | OD = 8.07 | Lf/ml = 60 |

Example IV

*Neisseria meningitidis* are non motile gram negative cocci, most often growing in pairs but occasionally in tetrads or clusters. They have antiphagocytic polysaccharides capsules which is the basis for serogroups.

Materials and Methods

Bacteria Strain

*Neisseria meningitidis*. C11

Media and Supplements

Preparation of the media involves use of different solutions as follows:

| "Franz medium" Preparation<br>Inoculum Shake Flask Medium Preparation | |
|---|---|
| Component | Amount per liter |
| Purified water | 800 mL |
| Glutamic acid | 1.6 g |
| $Na2HPO_42H2O$ | 15.5 g |
| KCl | 0.09 g |
| NH4Cl | 1.25 g |
| Purified water | QS to 1.0 liter |
| 3N NaOH | as required for pH = 7.6 |

Dissolve the above components with mixing. Sterilize by autoclaving at 121° C., 30 minutes. After cooling, the "50% Glucose" and "Men C Supplements" are added as below.

| | |
|---|---|
| "50% Glucose" | 10 mL/L +/− 0.3 mL |
| "Men C Fermentation Supplements" | 20 mL/L +/− 0.3 mL |

With the addition of the glucose and supplements solutions, the medium can be called "Franz Complete medium".

Preparation of the 20 L Fermenter

A. The Following Components Must be Introduced to a Mixing Vessel and Dissolved to Create 20 L of Watson Base Medium with CAA:

| Component | Amount per liter |
| --- | --- |
| Purified water | 800 mL |
| Glutamic acid | 1 g +/− 0.01 g |
| Na$_2$HPO$_4$2H$_2$O | 3.25 g +/− 0.03 g |
| KCl | 0.09 g +/− 0.001 g |
| Casamino acid | 10 g +/− 0.1 g |
| Purified water | QS to 1.0 liter |
| 3N NaOH | as required for pH = 7.6 |

A.A The Following Components Must be Introduced to a Mixing Vessel and Dissolved to Create 20 L of Watson Base Medium with Amisoy:

| Component | Amount per liter |
| --- | --- |
| Purified water | 800 mL |
| Glutamic acid | 1 g +/− 0.01 g |
| Na$_2$HPO$_4$2H$_2$O | 3.25 g +/− 0.03 g |
| KCl | 0.09 g +/− 0.001 g |
| Amisoy | 10 g +/− 0.1 g |
| Purified water | QS to 1.0 liter |
| 3N NaOH | as required for pH = 7.6 |

B. Fermenter Sterilization

Sterilize the fermenter for 25 minutes at 121° C. After sterilization, set the following conditions: temperature, 35° C.; aeration at 10 L/minute; agitation at 150 rpm, and backpressure at 0.2 bar. After cooling the fermenter to 35° C., and take a sample to measure pH, adjust the fermenter pH probe calibration and then adjust the medium pH to 7.6.

| C. Post-Sterilization Adjustments | |
| --- | --- |
| 1. Add "50% Glucose" | 10 ml/L |
| 2. Add "Men C Supplement" | 20 ml/L |

Medium with 1 + 2 above: "Watson Complete medium"

| A. "50% Glucose" Solution | |
| --- | --- |
| Component | Amount per liter |
| glucose (anhydrous) | 500 g +/− 5 g |
| Purified water | QS to 1.0 L |

This solution is sterilized by autoclaving at 121° C. for 30 minutes.

B. "Men C Supplements" Solution

| B.1 Ultrafiltered YE | |
| --- | --- |
| Component | Amount |
| Purified water | QS to 1 L |
| Yeast Extract | 125 g/L |

This solution is ultrafiltered through a 10 kD TFF apparatus.

The retentate is discarded after the requisite permeate has been collected, and the permeate is added to the vessel containing the supplement.

| B.2 | |
| --- | --- |
| Component | Amount per liter of UF YE |
| MgSO$_4$—7 H$_2$O | 30 g +/− 0.5 g |
| L-cystein-HCl | 1.5 g +/− 0.2 g |

Add the chemicals to 1 L UF YE, mix for 10 minutes, filter sterilized through a 0.2 micron filter and transfer to the fermenter.

C. 3 NNaOH

3N NaOH=12%(w/v)NaOH=120 g/L NaOH

D. Antifoam

The antifoam used is Dow Corning 1510. It is sterilized by autoclaving at 121° C. for 30 minutes Growth in Liquid Media A 500 milliliter flask is inoculated with 1.0 mL of a working stock vial. The shake flask contains 150 mL of complete "Franz medium".

The inoculated shake flasks is placed in an (1 inch throw) incubator-shaker at 35±1° C. at 150 rpm. After 10 hours, the flask is aseptically sampled. The optical density should be between 1.3-3.3 (at 590 nm) if so, the four 2 L shake flasks are each inoculated with the appropriate volume from the 150 mL shake flask.

Each 2 L shake flask contains 0.2 L of pre-warmed "Franz Complete medium".

The shake flasks are placed in an (1 inch throw) incubator-shaker at 35±1° C. at 200 rpm. After 10 hours, the contents of each shake flask are transferred into the sterile inoculation can and inoculate the fermenter.

Culture Vessel and Growth Conditions

Batch fermentations were carried out in 30 liters bioreactors (MBR Bioreactors A G, 8620 Wetzikon, C H) containing 20 L of medium.

The cultures were growing at 35° C. and 14×10$^3$ N/m$^2$ (2 psi) back pressure. The pH was controlled to 7.3 with 3 N NaOH. The initial agitation rate was set at minimum of 150 rpm, and bottom aeration at 10 L/minute. DOT was maintained at 35% by rpm control in a range 150-400, then supplementing with oxygen if necessary. Antifoam was added manually to control foaming. Residual concentration of glucose was detected and when it was around 2 g/L, 0.2 liters of glucose solution were added.

Biomass Determination.

Growth was monitored by optical density at 590 nm against a water blank (Perkin Elmer 35 spectrophotometer), light path of 1 cm. Purity checks of the samples were made by Gram staining.

Analysis of MenC PS

Quantitative estimation of the polysaccharides was performed analyzing the sialic acid content according to the method reported in Biochimica and Biophysica Acta (1957), 21, 610, by Lars Svennerholm.

Results

The growth curves obtained with Amisoy and with Casamino acids are compared in FIG. 8. The yield in MenC PS was 307 mg/L and 345 mg/L in the media containing Amisoy and Casamino acids respectively. The growth curves and PS production are quite similar using the two media.

It will be understood that the invention is described above by way of example only and modifications may be made within the scope of the invention as defined in the appended claims.

Example V

*Clostridium tetani* is a slender bacillus measuring 2 μm in length and 0.3-0.5 μm in width. It often exists in the form of a rather long filament-like cell. When spores are formed, the bacillus assumes the characteristic drumstick appearance. It is a mobile organism, gram positive, but its gram stain can become variable or even negative in aging cultures. *Clostridium tetani* is a strict anaerobe and produces two exotoxins. One of these, the tetano spasmin, is a neurotoxin responsible for the whole clinical picture of the disease.

Materials and Methods

Bacterial Strain

*Clostridium tetani* Harvary Y-VI-3.

Media

The seed cultures were prepared using the medium reported below expressed in g/L:

| Component | Amount g/L |
| --- | --- |
| N-Z Soy | 15.0 |
| Glucose | 5.5 |
| Yeast extract | 5.0 |
| NaCl | 2.5 |
| L-Cysteine | 0.5 |
| Sodium thioglycollate | 0.5 |
| Agar | 0.75 |

PH = 7.1

The production media were prepared as modification of the Mueller-Miller medium described in the WHONSQ/GEN/94 (1990). In this medium, beef heart infusion and casein solution are used, in the modified media reported below, expressed in g/L, Hysoy and Soytone were used instead of beef heart infusion and casein solution:

| Component | Amount g/L |
| --- | --- |
| Glucose-$H_2O$ | 12.1 |
| NaCl | 2.5 |
| $Na_2HPO_4$—$12H_2O$ | 2.5 |
| $KH_2PO_4$ | 0.15 |
| $MgSO_4$—$7H_2O$ | 0.15 |
| Amino acids solution | 17.5 ml |
| Vitamine solution | 4.2 ml |
| NaOH 5M | 4.0 ml |
| $FeSO_4$—$7H_2O$ (1% sol.) | 4.0 ml |
| Soy derivatives | 20.0 |

PH = 7.3

Sterilised by autoclaving at 120° C. for 20 min

Amino Acids Solution:

| Component | |
| --- | --- |
| L-Tyrosine | 28.51 g/L |
| Uracil- | 0.142 g/L |
| L-Cystein- | 14.25 g/L |
| HCl 37% | 131.6 ml/L |

Vitamin Solution:

| Component | |
| --- | --- |
| Ca pantithenate | 238.1 mg/L |
| Thiamine | 59.7 mg/L |
| Pyridoxin | 59.7 mg/L |
| Riboflavin | 59.7 mg/L |
| Biotin | 0.73 mg/L |
| Ethanol | 256.4 ml/L |

Growth in Liquid Media

Two 25 ml tubes, containing 15 ml of seed medium, were inoculated with 0.5 ml each of working seed vial and incubated at 35° C. for 29 hrs in anaerobic jar where a Gas generating kit (OXOID) was used. A second series of tubes were inoculated by 1.5 ml of the first tubes and incubated in the same conditions reported above for 24 hrs.

7 ml of these cultures were used to inoculate 100 ml tubes containing 75 ml of the same medium. These tubes were incubated in the same conditions reported above for 24 hrs.

The entire content of these tubes were used to inoculate 5000 ml beakers containing 2500 ml of the production medium.

Biomass Determination

Growth was monitored by optical density at 590 nm against a water blank (Pharmacia spectrophotometer), light path of 1 cm. Purity checks of the samples were made by Gram staining.

Results

After 186 hrs of incubation, the OD and the Lf/ml in the breakers were:

| | | |
| --- | --- | --- |
| Medium with Hysoy | OD = 1.08 | Lf/ml = 60 |
| Medium with Soytone | OD = 0.74 | Lf/ml = 60 |
| Medium with beef heart infusion and casein solution | OD = 1.236 | Lf/ml = 60 |

Example VI

*Bordetella pertussis* is a gram negative coccobacillus about 0.5 μm in diameter and 0.5 to 2 μm in length. Its nutritional requirements are simple, and it does not utilize sugars. It is extremely sensitive to fatty acids and survives poorly without protective factors.

Materials and Methods

Bacterial Strain

*Bordetella pertussis* 9K/129G (Pizza, M., et al. (1989) Science, 246, 497-500).

Media

The seed and production cultures were prepared using CL medium (Imaizumi, A., et al. (1983) Infection and Immunity, 41 (3), 1138-1143) reported below expressed in g/L:

| Component | Amount g/L |
| --- | --- |
| Sodium L-glutamate | 10.7 |
| L-proline | 0.24 |
| NaCl | 2.5 |
| $KH_2PO_4$ | 0.5 |
| KCl | 0.2 |
| $MgCl_2$—$6H_2O$ | 0.1 |
| $CaCl_2$ | 0.02 |
| Tris | 6.1 |
| L-Cysteine* | 0.04 |
| $FeSO_4$—$7H_2O$* | 0.01 |
| Niacin* | 0.004 |
| Glutathione reduced* | 0.15 |
| Ascorbic acid* | 0.4 |
| Casaminoacid | 10.0 |
| Dimethyl-B-cyclodextrin | 1.0 |

PH adjusted to 7.6 with HCl.

*sterilized by filtration and then added aseptically to the autoclaved medium The modified medium contained 10 g/l of N-Z soy instead of Casaminoacid.

Growth in Liquid Media 500 ml unbaffled shake flasks each with 100 ml of CL medium or the modified one, were inoculated with 3.0 mL of a working stock vial.

The shake flasks were placed in an (1" throw) incubator-shaker at 35±1° C. at 100 RPM for 12 hours. After 12 hours, the agitation was increased to 250 RPM for another 16 hours.

Biomass Determination

Growth was monitored by optical density at 590 mm against a water blank (Pharmacia spectrophotometer), light path of 1 cm. Purity checks of the samples were made by Gram staining.

Analysis of PT

This analysis was performed by ELISA (Nencioni, L., et al. (1990) Infect. Immun., 58, 1306-1315).

Results

After 28 hrs of incubation, the OD and PT (mg/L) in the flasks were:

| | | |
|---|---|---|
| medium with CAA. | OD = 2.31 | PT = 2.4 mg/L |
| Medium with NZ-soy. | OD = 1.99 | PT = 2.25 mg/L |

The invention claimed is:

1. A medium for cultivating *Haemophilus influenzae* to produce an immunogenic factor wherein the medium comprises a *Haemophilus influenzae* bacteria and at least about 50% by dry weight of a non-animal derived proteinaceous material, and which does not comprise animal derived proteinaceous material, wherein the non-animal derived proteinaceous material is a soybean derived protein composition.

2. A process for preparing an immunogenic factor of the *Haemophilus influenzae* bacteria comprising the steps of cultivating the *Haemophilus influenzae* bacteria in a medium comprising at least about 50% by dry weight of a non-animal derived proteinaceous material, wherein the medium does not comprise animal derived proteinaceous material and the non-animal derived proteinaceous material is a soybean derived protein composition.

3. The method of claim 2, further comprising purifying the immunogenic factor from the medium.

4. A process for the production of a vaccine comprising preparing an immunogenic factor of *Haemophilus influenzae* by the process of claim 3, and bringing said factor, optionally toxoided, into association with a pharmaceutically acceptable carrier.

* * * * *